(12) United States Patent
Su et al.

(10) Patent No.: US 11,931,467 B2
(45) Date of Patent: *Mar. 19, 2024

(54) ALBUMIN PHARMACEUTICAL COMPOSITION AND PREPARATION METHOD THEREFOR

(71) Applicant: SICHUAN KELUN PHARMACEUTICAL RESEARCH INSTITUTE CO., LTD., Chengdu (CN)

(72) Inventors: Zhengxing Su, Chengdu (CN); Likai Yang, Chengdu (CN); Dong Zhao, Chengdu (CN); Yujun Wang, Chengdu (CN); Fengying Shan, Chengdu (CN); Kexing Wang, Chengdu (CN); Lichun Wang, Chengdu (CN); Jingyi Wang, Chengdu (CN)

(73) Assignee: Sichuan Kelun Pharmaceutical Research Institute Co., Ltd., Chengdu (CN)

( * ) Notice: Subject to any disclaimer, the term of this patent is extended or adjusted under 35 U.S.C. 154(b) by 195 days.

This patent is subject to a terminal disclaimer.

(21) Appl. No.: 17/477,799

(22) Filed: Sep. 17, 2021

(65) Prior Publication Data

US 2022/0000792 A1    Jan. 6, 2022

Related U.S. Application Data

(62) Division of application No. 16/321,591, filed as application No. PCT/CN2017/102772 on Sep. 21, 2017, now Pat. No. 11,154,511.

(30) Foreign Application Priority Data

Sep. 29, 2016 (CN) .......................... 201610864142.1

(51) Int. Cl.
*A61K 9/51* (2006.01)
*A61K 9/19* (2006.01)
*A61K 31/337* (2006.01)

(52) U.S. Cl.
CPC .............. *A61K 9/5169* (2013.01); *A61K 9/19* (2013.01); *A61K 31/337* (2013.01)

(58) Field of Classification Search
CPC ....... A61K 9/5169; A61K 9/19; A61K 31/337
See application file for complete search history.

(56) References Cited

U.S. PATENT DOCUMENTS

| 5,641,803 | A | 6/1997 | Canetta et al. |
|---|---|---|---|
| 10,493,054 | B2 | 12/2019 | Su et al. |
| 2018/0028486 | A1 | 2/2018 | Su et al. |

FOREIGN PATENT DOCUMENTS

| CN | 101357126 A | 2/2009 |
|---|---|---|
| CN | 101361731 A | 2/2009 |
| CN | 101658516 A | 3/2010 |
| CN | 101745103 A | 6/2010 |
| CN | 101954067 A | 1/2011 |
| CN | 102327230 A | 1/2012 |
| CN | 103202813 A | 7/2013 |
| CN | 103751107 A | 4/2014 |
| DK | 0584001 T3 | 8/1997 |

OTHER PUBLICATIONS

British J. of Anaestasia 104(3); 276-284 (2010).*
Chinese First Office Action, Application No. 201780047050.7, dated Oct. 10, 2020.
Chinese Second Office Action, Application No. 201780047050.7, dated Aug. 2, 2021.
Yu MW, eta al., "Stabilization of Human Albumin by Caprylate and Acetyltryptophanate," Vox Sang, 1984, vol. 47, Issue 1, pp. 28-40. [Full English, and Chinese version with translated abstract included].

* cited by examiner

*Primary Examiner* — Shirley V Gembeh
(74) *Attorney, Agent, or Firm* — MacMillan, Sobanski & Todd, LLC

(57) ABSTRACT

Disclosed herein is an albumin pharmaceutical composition, comprising albumin and at least one amino acid having a relative molecular mass of 145-175. Clinically, the albumin pharmaceutical composition can effectively reduce undesirable responses, such as rash, urticaria, anaphylaxis and possible immune responses in the human body caused by albumin polymers and dimers, thereby further ensuring the safety in clinical medication.

6 Claims, No Drawings

ALBUMIN PHARMACEUTICAL COMPOSITION AND PREPARATION METHOD THEREFOR

RELATED CASES

This application is a divisional application of U.S. application Ser. No. 16/321,591 filed Jan. 29, 2019 which is a U.S. National Phase Application submitted under 35 U.S.C. 371 based on International Application No. PCT/CN2017102772 filed Sep. 21, 2017 (published as WO/2018/059304 on Apr. 5, 2018), which claims the benefit of priority to Chinese Patent Application 201610864142.1 filed Sep. 29, 2016, each and all of which are hereby incorporated by reference in their entirety.

TECHNICAL FIELD

The present invention relates to an albumin pharmaceutical composition, and more particularly relates to an albumin nanoparticle pharmaceutical composition comprising an amino acid having a relative molecular mass of 145 to 175 or a salt thereof.

BACKGROUND ART

Albumin has been widely used as a nanoparticle drug delivery system, and is mainly used for the delivery of poor water-soluble drugs such as taxanes, docetaxel and the like. Paclitaxel is insoluble in water, in order to improve the solubility of paclitaxel and make it suitable for intravenous injection, Bristol-Myers Squibb Company mixed it with a surfactant (e.g., polyethoxylated castor oil) and about 50% anhydrous alcohol (as a carrier of paclitaxel). However, in addition to side effects per se, the presence of the surfactant and anhydrous alcohol also results in serious drawbacks, which mainly is strong anaphylactic reaction.

In order to eliminate the strong anaphylactic reaction, the European Patent EP-A-0584001 and U.S. Pat. No. 5,641,803 disclosed addition of other substances to paclitaxel pharmaceutical compositions. However, the substances, which are added to prevent the anaphylactic reaction, will introduce side effects caused by these substances themselves into the pharmaceutical compositions.

Further, as a first commercially available albumin nanoparticle formulation, paclitaxel-albumin nanoparticle Abraxane was approved in the United States in 2005 and was approved by the CFDA in 2008 to be used for the treatment of metastatic breast cancer. Abraxane has recently been approved to be used for the treatment of non-small cell lung cancer, pancreatic cancer, and the like, in the United States. In the preparation of Abraxane, an albumin derived from human blood is used. At present, researchers from different countries are trying to use human serum albumin to develop albumin nanoparticles of other drugs, such as docetaxel.

Generally speaking, the biggest advantage of the Abraxane in clinical is the elimination of the anaphylactic reaction caused by common paclitaxel injections due to the addition of auxiliaries like polyethoxylated castor oil, thereby greatly improving the safety of the product. However, in clinical applications, some patients are also found certain anaphylactic reactions to Abraxane. The primary cause is that the increase of albumin dimers and polymers formed during storage, resulting in undesirable responses in human body, such as rash, urticaria, anaphylactic reactions and possible immune responses. The increase of albumin dimers and polymers in the formulation may also result in easily aggregation of the formulation, which may affect the physical stability of the formulation ("Effect of caprylate and acetyltryptophan on stabilization of human albumin", Progress in Microbiology and Immunology, 1985).

At present, there is no quite effective method for inhibiting the formation of albumin dimers and polymers in an albumin nanoparticle pharmaceutical composition during storage.

Therefore, an urgent problem to be solved in the field is to develop an albumin nanoparticle composition and pharmaceutical formulation, which can effectively control the amounts of albumin dimers and/or polymers in the albumin pharmaceutical composition during storage, and reduce anaphylactic reaction in clinical applications so as to further ensure the safety in clinical medication.

CONTENTS OF THE PRESENT INVENTION

It is an object of the present invention to provide a method for improving the quality of an albumin pharmaceutical composition, comprising adding at least one amino acid having a relative molecular mass of 145-175 or a salt thereof during the preparation of the pharmaceutical composition, and the amino acid may be selected from one or more of arginine, histidine and lysine, preferably arginine and/or histidine, more preferably arginine; and the amino acid or the salt thereof inhibits the formation and/or the increase of albumin dimers during the preparation, storage and/or use of the pharmaceutical composition.

It is another object of the present invention to provide a method for controlling the increase of albumin dimers during the preparation, storage and/or use of an albumin pharmaceutical composition, comprising adding at least one amino acid having a relative molecular mass of 145-175 or a salt thereof during the preparation of the pharmaceutical composition, wherein the amino acid may be selected from one or more of arginine, histidine and lysine, preferably arginine and/or histidine, more preferably arginine.

In some embodiments, in the pharmaceutical composition, the albumin dimers are present in an amount of no greater than about 10%, more preferably, no greater than about 7%, most preferably, no greater than about 5%, of the total amount of the albumins.

In some embodiments, the above methods inhibit the formation and/or the increase of albumin polymers during the preparation, storage, and/or use of the pharmaceutical composition.

Preferably, in the pharmaceutical composition, the albumin polymers are present in an amount of no greater than about 6%, more preferably, no greater than about 4%, most preferably, no greater than about 2%, of the total amount of the albumins.

In some embodiments, the amino acid or the salt thereof of the present invention is added in an amount that can effectively inhibit the formation and/or the increase of albumin dimers in the composition.

It is another object of the present invention to provide a method for preparing a pharmaceutical composition, comprising dissolving a taxane compound in a suitable organic solvent to obtain a solution of the taxane compound; dissolving or diluting an albumin into an aqueous solvent to obtain an aqueous solution of the albumin; preparing an aqueous solution of an amino acid having a relative molecular mass of 145-175 or a salt thereof by using water for injection; and subjecting the solution of the taxane compound, the aqueous solution of the albumin and the aqueous solution of the amino acid having a relative molecular mass of 145-175 or the salt thereof to dispersive-mixing under high shear force, then ultrafiltration, sterilization by filtration, and optional lyophilization.

The method does not comprise a step of adding a lyoprotectant prior to the lyophilization, wherein the lyoprotectant is selected from one or more of trehalose, sucrose, maltose, lactose, and glycine.

It is another object of the present invention to provide use of an amino acid or a salt thereof for inhibiting the formation and/or the increase of albumin dimers in a pharmaceutical composition for a certain period of time, wherein the amino acid has a relative molecular mass of 145-175, and the amino acid may be selected from one or more of arginine, histidine and lysine, preferably arginine and/or histidine, more preferably arginine.

In some embodiments, at 20-38° C., preferably 22-30° C., more preferably 25° C., for a period of more than 6 months, preferably more than 1 year, more preferably 2 years, in the pharmaceutical composition, the albumin monomers remain in an amount of above 83% of the total amount of the albumins, the albumin dimers remain in an amount of below 8% of the total amount of the albumins, and the albumin polymers remain in an amount of below 5% of the total amount of the albumins, preferably, the albumin monomers remain in an amount of above 85% of the total amount of the albumins, the albumin dimers remain in an amount of below 5% of the total amount of the albumins, and the albumin polymers remain in an amount of below 5% of the total amount of the albumins; and/or, In some embodiments, at 50-65° C., preferably 58-62° C., more preferably 60° C., for a period of more than one week, in the pharmaceutical composition, the albumin monomers remain in an amount of above 80% of the total amount of the albumins, the albumin dimers remain in an amount of below 9% of the total amount of the albumins, and the albumin polymers remain in an amount of below 6% of the total amount of the albumins; preferably, the albumin monomers remain in an amount of above 88% of the total amount of the albumins, the albumin dimers remain in an amount of below 6% of the total amount of the albumins, and the albumin polymers remain in an amount of below 3% of the total amount of the albumins, more preferably, the albumin monomers remain in an amount of above 90% of the total amount of the albumins, the albumin dimers remain in an amount of below 5% of the total amount of the albumins, and the albumin polymers remain in an amount of below 2% of the total amount of the albumins.

It is another object of the present invention to provide a stable albumin pharmaceutical composition, comprising an albumin and at least one amino acid having a relative molecular mass of 145-175 or a salt thereof, and in the pharmaceutical composition, the albumin dimmers are present in an amount of no more than about 10%, preferably no more than about 7%, and more preferably no more than about 5%, of the total amount of the albumins, in at least one year.

In some embodiments, in the pharmaceutical composition, the albumin polymers are present in an amount of no more than about 6%, preferably no more than about 4%, more preferably no more than about 2%, of the total amount of the albumins, in at least one year.

In the present invention, the amino acid refers to an amino acid having a relative molecular mass of 145 to 175, and furthermore, the amino acid of the present invention refers to one or more selected from arginine, histidine and lysine, preferably arginine and/or histidine, more preferably arginine. The weight ratio of the amino acid or a salt thereof to albumin is from 0.1:1 to 10:1, more preferably from 0.2:1 to 5:1.

In some embodiments, the pharmaceutical composition comprises a taxane compound as an active ingredient.

In some embodiments, the pharmaceutical composition is an albumin nanoparticle pharmaceutical composition.

In some embodiments, the amino acid or the salt thereof is the sole stabilizer in the pharmaceutical composition, and the amino acid may be selected from one or more of arginine, histidine, and lysine, preferably arginine and/or histidine, more preferably arginine.

In some embodiments, the pharmaceutical composition is a lyophilized powder injection.

It is another object of the present invention to provide use of the pharmaceutical composition of the present invention in the manufacture of a medicament for treating a cancer.

In some embodiments, the cancer is selected from one or more of prostate cancer, colon cancer, breast cancer, head and neck cancer, pancreatic cancer, lung cancer, ovarian cancer, multiple myeloma, renal cell carcinoma, melanoma, liver cancer, gastric cancer, and kidney cancer.

It is another object of the present invention to provide an albumin nanoparticle pharmaceutical composition, comprising a taxane compound, an albumin and at least one amino acid having a relative molecular mass of 145-175 or a salt thereof, and the composition comprises albumin monomers in an amount of no less than about 80% of the total amount of the albumins, and/or albumin dimers in an amount of no more than about 10% of the total amount of the albumins, and/or albumin polymers in an amount of no more than about 6% of the total amount of the albumins, and the amino acid may be selected from one or more of arginine, histidine and lysine, preferably arginine and/or histidine, more preferably arginine.

In some embodiments, the amino acid having a relative molecular mass of 145-175 comprised in the albumin nanoparticle pharmaceutical composition of the present invention refers to one or more of arginine, histidine, and lysine, preferably arginine and/or histidine, more preferably arginine.

In some embodiments, the taxane compound used in the present invention is selected from one or more of paclitaxel, docetaxel, cabazitaxel, and derivatives thereof.

In some embodiments, the albumin used in the present invention is selected from one or more of recombinant albumin, animal serum albumin, and human serum albumin, preferably human serum albumin.

It is another object of the present invention to provide a pharmaceutical formulation, comprising the albumin nanoparticle pharmaceutical composition, wherein the formulation comprises albumin monomers in an amount of no less than about 80% of the total amount of the albumins, and/or albumin dimers in an amount of no more than about 10% of the total amount of the albumins, and/or albumin polymers in an amount of no more than about 6% of the total amount of the albumins.

In some embodiments, the pharmaceutical formulation further comprises one or more pharmaceutically acceptable carriers and/or adjuvants.

It is another object of the present invention to provide use of the albumin nanoparticle pharmaceutical composition in the manufacture of a medicament for treating a cancer. In some embodiments, the cancer is selected from one or more of prostate cancer, colon cancer, breast cancer, head and neck cancer, pancreatic cancer, lung cancer, ovarian cancer, multiple myeloma, renal cell carcinoma, melanoma, liver cancer, gastric cancer, and kidney cancer.

It is another object of the present invention to provide a method for stabilizing an albumin nanoparticle pharmaceutical composition comprising a taxane compound, comprising adding an appropriate amount of at least one amino acid having a relative molecular mass of 145-175 or a salt thereof, wherein the amino acid particularly refers to one or more amino acid selected from arginine, histidine, and lysine, preferably arginine and/or histidine, more preferably arginine. The addition of the amino acid or the salt thereof can reduce albumin dimers and/or polymers or inhibit the increase thereof. In the method of the present invention, the addition of the amino acid or the salt thereof can reduce the formation of albumin dimers and/or polymers, and improve the chemical stability of albumin nanoparticles, thereby fundamentally solving the problem of the physically and chemically instability of albumin nanoparticles, reducing the kinds and amount of impurities, reducing toxicity in vitro and in vivo, and improving safety for patients.

In some embodiments, the method comprises preparing an albumin nanoparticle composition comprising a taxane compound under high shear conditions, wherein an appropriate amount of at least one amino acid having a relative molecular mass of 145-175 or a salt thereof is added during the preparation, and the amino acid particularly refers to one or more amino acid selected from arginine, histidine, and lysine, preferably arginine and/or histidine, more preferably arginine.

In some embodiments, the method of the present invention comprises the steps of: dissolving the taxane compound in a suitable organic solvent to obtain the solution of the taxane compound; dissolving or diluting the albumin into an aqueous solvent to obtain an aqueous solution of the albumin; preparing the aqueous solution of the amino acid having a relative molecular mass of 145-175 or the salt thereof by using water (preferably, water for injection), wherein the amino acid particularly refers to one or more amino acid selected from arginine, histidine, and lysine, preferably arginine and/or histidine, more preferably arginine; and subjecting the solution of the taxane compound, the aqueous solution of the albumin and the aqueous solution of the amino acid having a relative molecular mass of 145-175 or the salt thereof to dispersive-mixing under high shear force, then ultrafiltration, sterilization by filtration, and optional lyophilization.

It is another object of the present invention to provide use of an amino acid having a relative molecular mass of 145 to 175 or a salt thereof for stabilizing an albumin nanoparticle pharmaceutical composition or a pharmaceutical formulation comprising the albumin nanoparticle pharmaceutical composition. The use according to the present invention comprises inhibiting the formation of albumin dimers and/or polymers in the albumin nanoparticle pharmaceutical composition or the pharmaceutical formulation comprising the albumin nanoparticle pharmaceutical composition during storage by using an appropriate amount of at least one amino acid having a relative molecular mass of 145-175 or a salt thereof. The amino acid particularly refers to one or more amino acid selected from arginine, histidine, and lysine, preferably arginine and/or histidine, more preferably arginine.

It is another object of the present invention to provide use of an amino acid having a relative molecular mass of 145-175 or a salt thereof in the preparation of an albumin nanoparticle pharmaceutical composition for reducing adverse reactions in a subject, wherein the albumin nanoparticle pharmaceutical composition comprises a taxane compound, and the pharmaceutical composition comprises albumin monomers in an amount of no less than about 80% of the total amount of the albumins, and/or albumin dimers in an amount of no more than about 10% of the total amount of the albumins, and/or albumin polymer in an amount of no more than about 6% of the total amount of the albumins.

The use according to the present invention can improve the chemical stability of albumin nanoparticles, thereby fundamentally solving the problem of the physical and chemical instability of albumin nanoparticles, reducing the kinds and amount of impurities, reducing toxicity in vitro and in vivo, and improving safety for patients.

The albumin nanoparticle composition or formulation of the present invention and the albumin nanoparticle composition prepared according to the preparation method of the present invention, can reduce one or more adverse reactions including, for example, rash, urticaria, anaphylactic reaction, and immune response.

SPECIFIC MODE FOR CARRYING OUT THE PRESENT INVENTION

In the present invention, the following terms have the following definitions.

As used herein, the term "about" refers to a range of numerical value modified by the term ±10%, preferably ±5%.

As used herein, the term "amount" refers to weight percentage.

As used herein, the term "relative molecular mass" refers to the mass of a molecule relative to $1/12$ of a carbon atom, with unit of one.

As used herein, the term "amino acid having a relative molecular mass of 145-175" refers to a natural amino acid having a relative molecular mass in the range of from 145 to 175, and the amino acid specifically includes lysine, glutamine, glutamic acid, methionine, histidine, phenylalanine, arginine; the amino acid is preferably selected form a basic amino acid such as lysine, histidine or arginine; most preferably arginine.

As used herein, the term "room temperature" refers to a temperature of from 20° C. to 38° C.

As used herein, the term "RRT" refers to a retention time relative to the retention time of albumin monomers retained in size exclusion chromatography-HPLC.

As used herein, the term "albumin monomer" refers to a single albumin molecule without an intermolecular disulfide bond.

As used herein, the term "albumin dimer" refers to an albumin species having a RRT of from about 0.86 to about 0.97 relative to the retention time of albumin monomers retained in size exclusion chromatography-HPLC.

As used herein or in the present invention, the term "albumin polymer" refers to the sum of all albumin species except for albumin monomers and dimers, i.e., albumin species having a RRT of from about 0.50 to about 0.85 relative to the retention time of albumin monomers retained in size exclusion chromatography-HPLC.

As used herein, the term "taxanes" or "taxane compounds" include any diterpene compounds that inhibit the depolymerization of tubulin, including those naturally occurring or synthetic, crystalline and/or non-crystalline compounds, and the examples include, but are not limited to, paclitaxel, docetaxel, and cabazitaxel as well as analogs, derivatives, and prodrug forms thereof. The analogs and/or derivatives may include alcohols, ethers, esters, amines, salts, amides, halides, sulfides of paclitaxel, docetaxel and cabazitaxel or mixtures of two or more thereof.

In view of the change in spatial structure of albumin nanoparticles due to embedding a drug, the present inventors have surprisingly found that the addition of an amino acid having a relative molecular mass of 145-175 (particularly the amino acid selected from one or more of arginine, histidine and lysine, preferably arginine and/or histidine, more preferably arginine) or a salt thereof can effectively inhibit the increase of albumin dimers and polymers during the storage of a corresponding albumin nanoparticle pharmaceutical composition, whereas addition of other amino acid (e.g., glycine, aspartic acid etc.) has little effect on the inhibition of the increase of albumin dimers and polymers during the storage of the albumin nanoparticle pharmaceutical composition. Further, the addition of the amino acid or the salt thereof according to the present invention can effectively inhibit the degradation of albumin monomers during the storage of the albumin pharmaceutical composition.

The inventors have also surprisingly found that, in an albumin nanoparticle pharmaceutical composition comprising a taxane compound, the addition of the amino acid may allow albumin monomers remain in an amount of no less than about 80% of the total amount of the albumins, and/or albumin dimers in an amount of no more than about 10%, and/or albumin polymers in an amount of no more than about 6%. For example, the addition of the amino acid, particularly arginine or a salt thereof, to a corresponding albumin nanoparticle pharmaceutical composition comprising paclitaxel may allow the content of the albumin monomers remain in above 80% of the total amount of the albumins, the albumin dimers below 8%, and the polymers below 5%, after a storage of 24 months at room temperature (e.g., 25° C.). An addition of the amino acid having a relative molecular mass of 145-175, particularly arginine or the salt thereof, to a corresponding albumin nanoparticle pharmaceutical composition comprising docetaxel may allow the content of the albumin monomers remain above 85% of the total amount of the albumins, the albumin dimers below 5%, and albumin polymers below 5%, after a storage of 24 months at room temperature (e.g., 25° C.).

Based on the above discoveries, the present invention provides an albumin nanoparticle pharmaceutical composition, comprising a taxane compound, an albumin and at least one amino acid having a relative molecular mass of 145-175 (particularly the amino acid selected from one or more of arginine, histidine and lysine, preferably arginine and/or histidine, more preferably arginine) or a salt thereof as a stabilizer, wherein the composition comprises albumin monomers in an amount of no less than about 80% of the total amount of the albumins, and/or albumin dimers in an amount of no more than about 10% of the total amount of the albumins, and/or albumin polymers in an amount of no more than about 6% of the total amount of the albumins.

In some embodiments, the albumin nanoparticle pharmaceutical composition of the present invention comprises albumin monomers in an amount of no less than about 80%, about 85%, about 87%, about 90%, about 92%, about 93% or higher, of the total amount of the albumins.

In some embodiments, the albumin nanoparticle pharmaceutical composition of the present invention comprises albumin dimers in an amount of no more than about 10%, about 8%, about 6%, about 5% or less, of the total amount of the albumins.

In some embodiments, the albumin nanoparticle pharmaceutical composition of the present invention comprises albumin polymers in an amount of no more than about 6%, about 4%, about 2% or less, of the total amount of the albumins.

In some embodiments, the albumin nanoparticle pharmaceutical composition of the present invention comprises albumin monomers in an amount of no less than about 80%, and/or albumin dimers in an amount of no more than about 9%, and/or albumin polymers in an amount of no more than about 6%, of the total amount of the albumins.

In some embodiments, the albumin nanoparticle pharmaceutical composition of the present invention comprises albumin monomers in an amount of no less than about 83%, and/or albumin dimers in an amount of no more than about 8%, and/or albumin polymers in an amount of no more than about 5%, of the total amount of the albumins.

In some embodiments, the albumin nanoparticle pharmaceutical composition of the present invention comprises albumin monomers in an amount of no less than about 85%, and/or albumin dimers in an amount of no more than about 5%, and/or albumin polymers in an amount of no more than about 5%, of the total amount of the albumins.

In some embodiments, the albumin nanoparticle pharmaceutical composition of the present invention comprises albumin monomers in an amount of no less than about 88%, and/or albumin dimers in an amount of no more than about 6%, and/or albumin polymers in an amount of no more than about 3%, of the total amount of the albumins.

In some embodiments, the albumin nanoparticle pharmaceutical composition of the present invention comprises albumin monomers in an amount of no less than about 90%, and/or albumin dimers in an amount of no more than about 5%, and/or albumin polymers in an amount of no more than about 2%, of the total amount of the albumins.

The amino acid used in the present invention is selected from one or more of arginine, histidine and lysine, preferably arginine and/or histidine, more preferably arginine.

A salt of the amino acid according to the present invention may also achieve the same or similar effects as that achieved by the amino acid. The salt of the amino acid includes an inorganic acid salt and an organic acid salt, for example, but is not limited to, hydrochloride, sulfate, nitrate etc., as well as carboxylate (e.g., formate, acetate), sulfonate, and the like. Examples of the salt of the amino acid according to the present invention includes, but is not limited to, arginine hydrochloride, arginine nitrate, histidine hydrochloride, histidine sulfate, histidine acetate, lysine sulfonate, lysine sulfate, and the like. In the present invention, the amount of a salt of an amino acid is expressed by the amount of the amino acid after conversion.

The taxane compound used in the present invention is selected from one or more of paclitaxel, docetaxel, cabazitaxel, and derivatives thereof.

The albumin used in the present invention is selected from one or more of recombinant albumin, animal serum albumin, and human serum albumin, preferably human serum albumin.

In some embodiments, the human serum albumin used in the present invention may comprise a stabilizer such as sodium octanoate and/or a salt of acetyltryptophan etc. In other embodiments, the human serum albumin used in the present invention may be substantially free of stabilizers such as sodium octanoate and/or salts of acetyltryptophan etc.

The source of the albumin used in the present invention is not limited, and any modification or improvement of albumin is not required.

In some embodiments, in addition to the amino acid, other stabilizer such as sodium octanoate and/or a salt of acetyl tryptophan may be added to the albumin nanoparticle pharmaceutical composition of the present invention.

In some embodiments, the amino acid or the salt thereof is the sole stabilizer of the albumin nanoparticle pharmaceutical composition of the present invention.

In some embodiments, the albumin nanoparticle pharmaceutical compositions of the present invention are substantially free of lyoprotectants.

In some embodiments, the weight ratio of the amino acid or the salt thereof to the albumin in the albumin nanoparticle pharmaceutical composition of the present invention may be from 0.1:1 to 10:1, or from 0.15:1 to 8:1, or from 0.2:1 to 5:1, or from 0.25:1 to 4:1, or from 0.3:1 to 3:1, or from 0.4:1 to 2:1, or from 0.5:1 to 1:1.

In some embodiments, the weight ratio of the amino acid having a relative molecular mass of 145-175 or the salt thereof to the taxane compound in the albumin nanoparticle pharmaceutical composition of the present invention may be no more than 80:1, or from 2:1 to 60:1, or from 3:1 to 50:1, or form 3:1 to 20:1, or from 3:1 to 15:1, or the like. In some embodiments, the weight ratio of the amino acid or the salt thereof to the taxane compound in the albumin nanoparticle pharmaceutical composition of the present invention may range from 3:1 to 20:1, such as about 4.5:1, about 7.5:1, about 11.25:1, and the like.

In some embodiments of the albumin nanoparticle pharmaceutical composition comprising docetaxel according to the present invention, the weight ratio of the amino acid (e.g., arginine) or the salt thereof to docetaxel may range from 2:1 to 50:1, or from 3:1 to 30:1, or from 3:1 to 20:1, or from 4:1 to 25:1, or from 4:1 to 20:1, or from 5:1 to 20:1, or from 8:1 to 20:1, or from 10:1 to 15:1 etc., for example, about 11.25:1.

In some embodiments of the albumin nanoparticle pharmaceutical composition comprising paclitaxel according to the present invention, the weight ratio of the amino acid (e.g., arginine or histidine) or the salt thereof to paclitaxel may be from 2:1 to 50:1, or from 2:1 to 30:1, or from 3:1 to 20:1, or from 3:1 to 15:1, or from 3:1 to 10:1 etc., for example, about 4.5:1.

In some embodiments of the albumin nanoparticle pharmaceutical composition comprising cabazitaxel according to the present invention, the weight ratio of the amino acid or the salt thereof (e.g., arginine hydrochloride) to cabazitaxel may be from 1:1 to 50:1, or from 2:1 to 30:1, or from 3:1 to 25:1, or from 4:1 to 20:1, or from 5:1 to 15:1 etc., for example, about 7.5:1.

In some embodiments, in the albumin nanoparticle pharmaceutical composition according to the present invention, the weight ratio of the amino acid or the salt thereof to the albumin may be from 0.1:1 to 10:1, or from 0.15:1 to 8:1, or from 0.2:1 to 5:1, or from 0.25:1 to 4:1, or from 0.3:1 to 3:1, or from 0.4:1 to 2:1, or from 0.5:1 to 1:1, and the weight ratio of the amino acid or the salt thereof to the taxane compound may be no more than 80:1, for example, from 2:1 to 60:1, or from 3:1 to 50:1, or from 3:1 to 20:1, or from 4:1 to 15:1 etc., for example, about 4.5:1, or about 7.5:1, or about 11.25:1, and the like.

In some embodiments, the albumin nanoparticle pharmaceutical composition according to the present invention comprises paclitaxel, a human serum albumin, and arginine and/or histidine, wherein the weight ratio of the arginine and/or histidine to the human serum albumin is from 0.2:1 to 5:1, preferably from 0.3:1 to 3:1, and the weight ratio of arginine and/or histidine to paclitaxel is from about 3:1 to 20:1, preferably from 3:1 to 10:1.

In some embodiments, the albumin nanoparticle pharmaceutical composition according to the present invention comprises docetaxel, a human serum albumin, and arginine, wherein the weight ratio of arginine to the human serum albumin is from 0.2:1 to 5:1, preferably from 0.3:1 to 3:1, and the weight ratio of arginine to docetaxel is from about 3:1 to 20:1, preferably from 5:1 to 20:1.

In some embodiments, the albumin nanoparticle pharmaceutical composition according to the present invention comprises cabazitaxel, a human serum albumin, and arginine hydrochloride, wherein the weight ratio of the arginine hydrochloride (expressed by the weight of arginine) to the human serum albumin is from 0.2:1 to 5:1, preferably from 0.3:1 to 3:1, and the weight ratio of arginine hydrochloride (expressed by weight of arginine) to cabazitaxel is about from 3:1 to 20:1, preferably from 5:1 to 15:1.

The nanoparticle of the albumin nanoparticle pharmaceutical composition of the present invention has an average particle diameter of not more than 200 nm. In some embodiments, the nanoparticle of the albumin nanoparticle pharmaceutical composition of the present invention has an average particle size of not more than 160 nm. In some embodiments, the nanoparticle of the albumin nanoparticle pharmaceutical composition of the present invention has an average particle size of no more than 130 nm. In some embodiments, the nanoparticle of the albumin nanoparticle pharmaceutical composition of the present invention has an average particle size of not more than 110 nm. In some embodiments, the nanoparticle of the albumin nanoparticle pharmaceutical composition of the present invention has an average particle size of, for example, about 95 nm, about 100 nm, about 110 nm, about 120 nm.

The albumin nanoparticle composition of the present invention comprises one or more of the above characteristics.

It is an object of the present invention to provide a method for stabilizing albumin nanoparticle, comprising reducing albumin dimers and/or polymers or inhibiting their formation/increase by using an appropriate amount of at least one amino acid having a relative molecular mass of 145-175 (particularly the amino acid selected from one or more of arginine, histidine and lysine, preferably arginine and/or histidine, more preferably arginine) or a salt thereof. The method of the present invention, comprising using the amino acid or the salt thereof, thereby reducing the formation of albumin dimers and/or polymers, improving the chemical stability of albumin nanoparticle, consequently solving the problem of the physical and chemical instability of albumin nanoparticle fundamentally, reducing the types and amount of impurities, reducing toxicity in vitro and in vivo, improving the applicability in patients.

Emulsification through high pressure homogenization or the like is applied in the method of the present invention, which comprises adding an appropriate amount of the amino acid of the present invention or the salt thereof during the preparation of albumin nanoparticle comprising a drug and a carrier of albumin under high shear condition.

The present invention particularly provides a method for preparing an albumin nanoparticle pharmaceutical composition, comprising dispersing a taxane compound in an organic solvent to obtain an organic phase, dispersing an albumin in an aqueous solvent to obtain an aqueous phase, dispersive-mixing the organic phase and the aqueous phase under high shear force to obtain a nanoparticle solution, adding a solution of the amino acid of the present invention in the above procedure to obtain a resulting solution, and subjecting the resulting solution to sterilization by filtration and optional lyophilization to obtain the albumin nanoparticle pharmaceutical composition or lyophilized formulation thereof.

The present invention particularly provides a preparation method, comprising the following steps: dissolving a taxane compound in a suitable organic solvent to obtain a solution of a taxane compound; dissolving or diluting an albumin into an aqueous solvent to obtain an aqueous solution of albumin; preparing an aqueous solution of an amino acid having a relative molecular mass of 145-175 or a salt thereof by using water (preferably, water for injection), wherein the amino acid particularly refers to one or more amino acid selected from arginine, histidine, and lysine, preferably arginine and/or histidine, more preferably arginine; and subjecting the solution of the taxane compound, the aqueous solution of the albumin and the aqueous solution of the amino acid having a relative molecular mass of 145-175 or the salt thereof to dispersive-mixing under high shear force, then ultrafiltration, sterilization by filtration, and optional lyophilization.

In some embodiments, a method for preparing the albumin nanoparticle pharmaceutical composition according to the present invention is provided, wherein the method comprising the steps of:

the taxane compound is dissolved in a suitable organic solvent (e.g., ethanol) to obtain a solution of the taxane compound; the albumin is dissolved or diluted into an aqueous solvent (e.g., water), and then incubated, for example, incubated in a water bath at a temperature of 55-75° C. for 3-15 minutes, to obtain an aqueous solution of the albumin (e.g., aqueous solution); an aqueous solution of the amino acid or the salt thereof (e.g., an aqueous solution having a pH of 6.5-7.5) of the present invention is prepared with an acid and/or base (e.g., hydrochloric acid and/or sodium hydroxide) as a pH regulator; the solution of taxane compound, the aqueous solution of the albumin and the aqueous solution of the amino acid or the salt thereof are subjected to dispersive-mixing under high shear force (for example, at 1000-8000 rpm) and then ultrafiltration to obtain a concentrated solution of the albumin nanoparticle; and the concentrated solution is sterilized by filtration and optionally lyophilized.

In the above process, the weight ratio of the amino acid or the salt thereof to albumin is from 0.1:1 to 10:1.

In the above preparation method, the water used is preferably water for injection.

A person skilled in the art can carry out the above steps in a different order to prepare the albumin nanoparticle pharmaceutical composition of the present invention. For example, the aqueous solution of the amino acid or the salt thereof, the solution of the taxane compound, and the aqueous solution of the albumin can be prepared separately, and the aqueous solution of the amino acid or the salt thereof, the aqueous solution of the albumin, and the solution of the taxane compound are mixed under high shear force, then ultrafiltered, sterilized by filtration, and consequently lyophilized.

When the method of the present application is applied, it is not necessary to add a lyoprotectant, such as one or more lyoprotectants selected from trehalose, sucrose, maltose, lactose and glycine, prior to the lyophilization.

The amino acid or the salt thereof is added to the albumin nanoparticle pharmaceutical composition by the preparation method of the present invention to obtain the albumin nanoparticle pharmaceutical composition having satisfactory effect in inhibiting the increase of albumin dimers and polymers, as well as in inhibiting the degradation of albumin monomers.

In another aspect, the present invention provides a pharmaceutical formulation comprising the albumin nanoparticle pharmaceutical composition of the present invention.

In some embodiments, the pharmaceutical formulation of the present invention may further comprise a second active ingredient/second therapeutic agent. The second active ingredient/second therapeutic agent used in the present invention may include, but is not limited to, an anthracycline drug (e.g., epirubicin), a nucleoside compound (e.g., gemcitabine), and the like.

In some embodiments, the pharmaceutical formulation of the present invention further comprises one or more pharmaceutically acceptable carriers and/or adjuvants.

In some embodiments, the pharmaceutically acceptable carrier and/or adjuvant used in the present invention include sterile water, saline, dextrose, oil (e.g., corn oil, peanut oil, sesame oil, and the like), acid, lower alkanols (glycol; polyalkylene glycol). In other embodiments, the pharmaceutically acceptable carrier and/or adjuvant used in the present invention may also include preservatives, wetting agents, emulsifying agents, penetration enhancers, and the like.

For example, in some embodiments, the composition/pharmaceutical formulation of the present invention may further comprise an antimicrobial agent (e.g., a chelating agent, which includes, but is not limited to, EDTA, edetate (ester), citrate(ester), pentetate(ester), tromethamine, sorbate(ester), ascorbate(ester), a derivative thereof, or a mixture thereof; e.g., a non-chelating agent, which includes, but is not limited to, any one or more of sulfite, benzoic acid, benzyl alcohol, chlorobutanol and paraben), a sugar (e.g., sucrose, and the like), other reconstruction enhancer (such as those described in US. Patent Application having a publication number of 2005/0152979, and all contents of which are incorporated herein by reference), a negatively charged component (e.g., bile salts, bile acids, glycocholic acid, cholic acid, chenodeoxycholic acid, taurocholic acid, glycochenodeoxycholic acid, taurochenodeoxycholic acid, lithocholic acid, ursodeoxycholic acid, dehydrocholic acid, phospholipids).

In some embodiments, the pharmaceutical formulation of the present invention is a lyophilized powder injection. The nanoparticle pharmaceutical composition of the present invention can be prepared into lyophilized powder injection by a preparation method well known in the art.

The albumin nanoparticle pharmaceutical composition of the present invention can be used for treating a cancer, including, but not limited to, one or more selected from the group consisting of prostate cancer, colon cancer, breast cancer (e.g., metastatic breast cancer), head and neck cancer, pancreatic cancer (e.g., metastatic pancreatic cancer or locally advanced non-resectable pancreatic cancer), lung cancer (e.g., non-small cell lung cancer), ovarian cancer, multiple myeloma, renal cell carcinoma, melanoma (e.g., metastatic melanoma), liver cancer, gastric cancer, and kidney cancer.

The administration dose of the albumin nanoparticle pharmaceutical composition of the present invention may vary depending on a particular taxane compound, administration method, and particular type of the cancer to be treated. This dose is sufficient to produce the desired benefits. The compositions can be formulated for single- or multiple-dose administration.

The albumin nanoparticle pharmaceutical composition or pharmaceutical formulation of the present invention can be administered by any route known to a person skilled in the art, including intramuscular, intravenous, intradermal, intralesional, intraperitoneal injection or any other suitable route. The administration can be topical, topical or systemic administration, depending on a site to be treated. The most appropriate route in any given situation depends on a variety of factors, such as the nature, progression and severity of a disease, and the like. In some embodiments, the pharmaceutical composition or pharmaceutical formulation of the present invention is administered by intravenous injection.

In some embodiments, the nanoparticle pharmaceutical composition or pharmaceutical formulation of the present invention may also be administered with a second active ingredient/second therapeutic agent. In some embodiments, the nanoparticle pharmaceutical composition or pharmaceutical formulation of the present invention can be administered simultaneously, sequentially or in parallel with the second active ingredient/second therapeutic agent. When administered separately, the nanoparticle pharmaceutical composition or pharmaceutical formulation of the present invention and the second active compound or second therapeutic agent can be administered at different frequency or interval of administration.

The second active ingredient/second therapeutic agent used in the present invention may include, but is not limited to, an anthracycline drug (e.g., epirubicin), a nucleoside compound (e.g., gemcitabine), and the like.

In another aspect, the present invention provides use of the albumin nanoparticle pharmaceutical composition or pharmaceutical formulation of the present invention in the manufacture of a medicament for the treatment of a disease associated with cell proliferation or cell hyperproliferation (e.g., cancer).

In some embodiments, the cancer includes, but is not limited to, one or more selected from the group consisting of prostate cancer, colon cancer, breast cancer (e.g., metastatic breast cancer), head and neck cancer, pancreatic cancer (e.g., metastatic pancreatic cancer or locally advanced non-resectable pancreatic cancer), lung cancer (e.g., non-small cell lung cancer), ovarian cancer, multiple myeloma, renal cell carcinoma, melanoma (e.g., metastatic melanoma), liver cancer, gastric cancer, and kidney cancer.

In some embodiments, the medicament is a lyophilized powder injection. The lyophilized powder injection can be re-formulated as a solution, an emulsion or a suspension for administration, or can be formulated into a colloid.

In another aspect, the invention provides use of an amino acid having a relative molecular mass of 145-175 (particularly the amino acid selected from one or more of arginine, histidine, and lysine, preferably arginine and/or histidine, more preferably arginine) or a salt thereof for inhibiting the content of albumin dimers and/or polymers in an albumin nanoparticle pharmaceutical composition (particularly the albumin nanoparticle pharmaceutical composition of the present invention) during storage. In some embodiments, the weight ratio of the amino acid having a relative molecular mass of 145-175 or the salt thereof to albumin in the pharmaceutical composition is from 0.1:1 to 10:1, preferably from 0.2:1 to 5:1.

In some embodiments, the storage period may be 24 months for which the storage is performed at room temperature (e.g., 25° C.).

As compared with a composition without the addition of the amino acid or the salt thereof of the present invention, the taxane-albumin nanoparticle composition added with the amino acid or a salt thereof has significantly improved the albumin characteristics and a reduced polymerization rate of the albumin. This reduced ratio can be evaluated, for example, under conditions of long-term storage at room temperature (e.g., 25° C.) or under accelerated conditions at an elevated temperature (e.g., 60° C.).

In some embodiments, the addition of the amino acid, e.g., arginine, of the present invention or the salt thereof to the corresponding albumin nanoparticle pharmaceutical composition (e.g., an albumin nanoparticle pharmaceutical composition comprising paclitaxel) may allow albumin dimers and polymers to be controlled at no more than about 8% and about 5% of the total amount of the albumins, respectively, and albumin monomers to be maintained at no less than 83% of the total amount of the albumins, under conditions of 24 months storage at room temperature (e.g., 25° C.).

In some embodiments, the addition of the amino acid, e.g., arginine, of the present invention or the salt thereof to the corresponding albumin nanoparticle pharmaceutical composition (e.g., an albumin nanoparticle pharmaceutical composition comprising docetaxel) may allow both of albumin dimers and polymers to be controlled at no more than about 5% of the total amount of the albumins, respectively, and albumin monomers to be maintained at no less than 85% of the total amount of the albumins, under conditions of 24 months storage at room temperature (e.g., 25° C.).

In some embodiments, the addition of the amino acid, e.g., histidine, of the present invention or the salt thereof to the corresponding albumin nanoparticle pharmaceutical composition (e.g., an albumin nanoparticle pharmaceutical composition comprising paclitaxel) may allow albumin dimers and polymers to be controlled at no more than about 9% and about 6% of the total amount of the albumins, respectively, and albumin monomers to be maintained at no less than 80% of the total amount of the albumins, under conditions of 10 days storage at an elevated temperature (e.g., 60° C.).

In some embodiments, the addition of the amino acid, e.g., arginine, of the present invention or the salt thereof to the corresponding albumin nanoparticle pharmaceutical composition (e.g., an albumin nanoparticle pharmaceutical composition comprising paclitaxel) may allow albumin dimers and polymers to be controlled at no more than about 6% and about 3% of the total amount of the albumins, respectively, and albumin monomers to be maintained at no less than 88% of the total amount of the albumins, under conditions of 10 days storage at an elevated temperature (e.g., 60° C.).

In some embodiments, the addition of the amino acid, e.g., arginine, of the present invention or the salt thereof to the corresponding albumin nanoparticle pharmaceutical composition (e.g., an albumin nanoparticle pharmaceutical composition comprising cabazitaxel) may allow albumin dimers and polymers to be controlled at no more than about 5% and about 2% of the total amount of the albumins, respectively, and albumin monomers to be maintained at no less than 90% of the total amount of the albumins, under conditions of 10 days storage at an elevated temperature (e.g., 60° C.).

In another aspect, the present invention provides use of an amino acid having a relative molecular mass of 145-175 (particularly the amino acid selected form one or more of arginine, histidine, and lysine, preferably arginine and/or histidine, more preferably arginine) or a salt thereof in the manufacture an albumin nanoparticle pharmaceutical composition for reducing adverse reactions in a subject, wherein the albumin nanoparticle pharmaceutical composition comprises a taxane compound, and in the pharmaceutical composition, albumin monomers is in an amount of no less than about 80% of the total amount of the albumins, and/or albumin dimers is in an amount of no more than about 10% of the total amount of the albumins, and/or albumin polymers is in an amount of no more than about 6% of the total amount of the albumins.

In some embodiments, the amino acid of the present invention or the salt thereof is used as a stabilizer, further as the sole stabilizer, in the albumin nanoparticle pharmaceutical composition. The beneficial effects of the present invention are as follows:
1. By adding the amino acid having a relative molecular mass of 145-175 (particularly the amino acid selected from one or more of arginine, histidine and lysine, preferably arginine and/or histidine, more preferably arginine) or the salt thereof to the albumin pharmaceutical composition, the degradation of albumin monomers and the increase of albumin dimers and polymers in the composition during storage is effectively inhibited, and the adverse reactions in clinical applications thereof, such as rash, urticaria, anaphylactic reaction and possible immune response, are effectively reduced, further ensuring the safety in clinical medication.
2. No additional stabilizer is required to be added, and there is no need to limit the source or make any modification or improvement to the albumin in the pharmaceutical composition; correspondingly, the raw material sources are wide and the preparation method is simple.

The present invention is further illustrated in the following examples. It is necessary to be noted that the following examples should not to be understood as any limitation of the protection scope of the present invention, and some non-essential improvements and adjustments to the present invention in light of the contents of the present invention described above made by a person skilled in the art still fall within the protection scope of the present invention.

The Abraxane used in the examples was a paclitaxel albumin nanoparticle formulation purchased from Celgene. The docetaxel, paclitaxel and cabazitaxel are active pharmaceutical ingredient, which are commercially available or can be prepared by methods well known to a person skilled in the art.

EXAMPLE 1

Preparation of a Docetaxel-Albumin Nanoparticle Composition by Using Arginine 9 g Arginine was weighed, then an appropriate amount of water for injection was added, the pH was adjusted to 6.8 with hydrochloric acid and/or NaOH, and then volumed to 30 ml to obtain a solution of arginine. Then, 0.8 g of docetaxel was added to a 100 ml beaker, followed by an addition of 20 ml of ethanol, and ultrasonically dissolved to obtain an organic phase comprising docetaxel. Human serum albumin was dissolved in water for injection to prepare a 4 mg/ml solution, and incubated in a water bath at 63° C. for 10 minutes to obtain an aqueous phase comprising human serum albumin. The organic phase comprising docetaxel was uniformly dispersed in the aqueous phase comprising human serum albumin under high-speed shear at 6,000 revolutions per minute (rpm), and the resulting dispersion was transferred to a device for concentration by ultrafiltration and ultrafiltered to obtain a docetaxel nanoparticle solution with a docetaxel concentration of 5 mg/ml. The solution of arginine was added to the docetaxel nanoparticle solution and stirred to obtain a docetaxel nanoparticle solution comprising arginine, and the docetaxel nanoparticle solution comprising arginine had an average particle size of 153 nm measured by Malvern Nano-ZS90 nanometer particle size analyzer. The prepared docetaxel nanoparticle solution comprising arginine was subjected to filtration sterilization with a 0.22 μm sterile filter, and lyophilized for 48 hours to remove ethanol and water for injection to obtain a powdery docetaxel-albumin nanoparticle composition.

EXAMPLE 2

Preparation of a Paclitaxel-Albumin Nanoparticle Composition by Using Arginine 4.5 g Arginine was weighed, then an appropriate amount of water for injection was added, the pH was adjusted to 7.0 with hydrochloric acid and/or NaOH, and then volumed to 15 ml to obtain a solution of arginine. Then, 1.0 g of paclitaxel was added to a 100 ml beaker, followed by an addition of 25 ml of ethanol, and ultrasonically dissolved to obtain an organic phase comprising paclitaxel. 9 g of human serum albumin was dissolved in water for injection to prepare a 6 mg/ml solution, and incubated in a water bath at 65° C. for 10 minutes to obtain an aqueous phase comprising human serum albumin. The organic phase comprising paclitaxel was uniformly dispersed in the aqueous phase comprising human serum albumin under high-speed shear at 3,000 revolutions per minute (rpm), and the dispersion was transferred to a device for concentration by ultrafiltration and ultrafiltered to obtain a paclitaxel nanoparticle solution with a paclitaxel concentration of 6 mg/ml. The solution of arginine was added to the paclitaxel nanoparticle solution and stirred to obtain a paclitaxel nanoparticle solution comprising arginine, and the paclitaxel nanoparticle solution comprising arginine had an average particle size of 123 nm measured by Malvern Nano-ZS90 nanometer particle size analyzer. The prepared paclitaxel nanoparticle solution comprising arginine was subjected to filtration sterilization with a 0.22 μm sterile filter, and lyophilized for 48 hours to remove ethanol and water for injection to obtain a powdery paclitaxel-albumin nanoparticle composition.

EXAMPLE 3

Preparation of a Paclitaxel-Albumin Nanoparticle Composition by Using Histidine

A paclitaxel-albumin nanoparticle composition of Example 3 was prepared by a method similar to that of Example 2 except that histidine was used as a stabilizer instead of arginine.

EXAMPLE 4

Preparation of a Cabazitaxel-Albumin Nanoparticle Composition by Using Arginine Hydrochloride 4.5 g Arginine hydrochloride by weight of arginine was weighed, then an appropriate amount of water for injection was added, the pH was adjusted to 6.8 with hydrochloric acid and/or NaOH, and then volumed to 10 ml to obtain a solution of arginine hydrochloride. Then, 0.6 g of cabazitaxel was added to a 100 ml beaker, followed by an addition of 20 ml of ethanol, and ultrasonically dissolved to obtain an organic phase comprising cabazitaxel. Human serum albumin was dissolved in water for injection to prepare a 4 mg/ml solution, and incubated in a water bath at 63° C. for 5 minutes to obtain an aqueous phase comprising human serum albumin. The solution of arginine hydrochloride was added to the aqueous phase comprising human serum albumin to obtain an aqueous phase comprising human serum albumin added with arginine hydrochloride. The organic phase comprising cabazitaxel was uniformly dispersed into the aqueous phase comprising human serum albumin added with arginine hydrochloride under high-speed shear at 3,000 revolutions per minute (rpm), and the dispersion was transferred to a device for concentration by ultrafiltration and ultrafiltered to be a cabazitaxel concentration of 5 mg/ml to obtain a cabazitaxel nanoparticle solution comprising arginine hydrochloride. The cabazitaxel nanoparticle solution comprising arginine hydrochloride had an average particle size of 106 nm measured by Malvern Nano-ZS90 nanometer particle size analyzer. The prepared cabazitaxel nanoparticle solution comprising arginine hydrochloride was subjected to filtration sterilization with a 0.22 μm sterile filter, and lyophilized for 48 hours to remove ethanol and water for injection to obtain a powdery cabazitaxel-albumin nanoparticle composition.

COMPARATIVE EXAMPLE 1

Preparation of a Docetaxel-Albumin Nanoparticle Composition without Arginine

A docetaxel albumin nanoparticle composition was prepared by a method similar to that of Example 1 except that the solution of arginine was not added.

COMPARATIVE EXAMPLE 2

Preparation of a Paclitaxel-Albumin Nanoparticle Composition without Arginine

A paclitaxel-albumin nanoparticle composition was prepared by a method similar to that of Example 2 except that the solution of arginine solution was not added.

COMPARATIVE EXAMPLE 3

Preparation of a Paclitaxel-Albumin Nanoparticle composition by Using Glycine

A paclitaxel-albumin nanoparticle composition was prepared by a method similar to that of Example 2 except that glycine was used instead of arginine.

COMPARATIVE EXAMPLE 4

Preparation of a Paclitaxel-Albumin Nanoparticle Composition by Using Aspartic Acid A paclitaxel-albumin nanoparticle composition was prepared by a method similar to that of Example 2 except that aspartic acid was used instead of arginine.

COMPARATIVE EXAMPLE 5

Preparation of a Cabazitaxel-Albumin Nanoparticle Composition without Arginine Hydrochloride A cabazitaxel-albumin nanoparticle composition was prepared by a method similar to that of Example 4 except that the solution of arginine hydrochloride was not added.

COMPARATIVE EXAMPLE 6

Preparation of a Cabazitaxel-Albumin Nanoparticle Composition by Using Sodium Octanoate as a Stabilizer A cabazitaxel-albumin nanoparticle composition was prepared by a method similar to that of Example 4 except that sodium octanoate was used instead of arginine.

COMPARATIVE EXAMPLE 7

Preparation of a Cabazitaxel-Albumin Nanoparticle Composition by Using Sodium Octanoate and Acetyl Tryptophan as Stabilizer A cabazitaxel-albumin nanoparticle composition was prepared by a method similar to that of Example 4 except that sodium octanoate and acetyl tryptophan (1:1) were used as a stabilizer instead of arginine.

TEST EXAMPLE 1

The increase tendency of albumin dimers and polymers as well as the degradation tendency of albumin monomers in the docetaxel-albumin nanoparticle composition prepared according to the methods described in Example 1 and Comparative Example 1 was observed in the study of long-term stability under conditions of 24 months storage at 25° C. The content of albumin monomers, dimers and polymers in the nanoparticle composition were analyzed by size exclusion chromatography.

Conditions of size exclusion HPLC were as follows:

Chromatographic conditions and system suitability test: a size exclusion chromatography containing hydrophilic silica gel (the chromatography column was: TOSOH TSK gel G3000SWxl, 300×7.8 mm 5 μm; and the guard column was: TOSOH TSK gel G3000 SWxl, 40×6.0 mm 7 μm) was employed, wherein a 0.2 mol/L and pH 7.0 phosphate buffer solution containing 1% isopropanol (the solution was obtained by mixing 200 ml of 0.5 mol/L sodium dihydrogen phosphate, 420 ml of 0.5 mol/L disodium hydrogen phosphate, 15.5 ml of isopropanol and 914.5 ml of water) was used as mobile phase; the test wavelength was 280 nm; the flow rate was 0.6 ml/min; and the column temperature was 30° C.

Determination method: an appropriate amount of a reference substance of human blood albumin was taken and diluted with water to prepare a solution containing about 6.4 mg, 3.2 mg, or 1.6 mg of albumin per 1 ml as a reference solution. 20 μl of each of the reference solutions was measured off and injected into the HPLC liquid chromatography, and the corresponding chromatograms were recorded. The linear regression equation was calculated from the concentration and peak area of the reference solution.

80 mg of each of the compositions obtained in Example 1 and Comparative Example 1 was taken as test samples and placed in a 25 ml volumetric flask, dissolved in water and diluted to the mark, and shaken well to prepare a solution with the albumin concentration of about 3 mg/ml. 20 μl of each of the test sample solutions was measured off, and injected into the HPLC liquid chromatograph, and the corresponding chromatograms were recorded. The content of monomers, dimers and polymers of human serum albumin in the test samples were calculated according to the regression equation.

Calculation Manner:

The content of albumin dimers refers to a percentage of the peak area with a retention time RRT of from about 0.86 to about 0.97 with respect to the entire peak area in the HPLC chromatogram.

The content of albumin polymers refers to a value obtained by dividing a percentage of the peak area with a retention time RRT of from about 0.50 to about 0.85 with respect to the entire peak area in the size exclusion HPLC chromatogram by two.

The content of albumin monomer was calculated using the following formula: albumin monomers %=1−2×albumin polymers %−albumin dimers %.

Test results were shown in Table 1.

TABLE 1

TABLE 1 contents of albumin monomers, dimers and polymers in the composition comprising arginine of Example 1 and in the composition without arginine of Comparative Example 1 in the study on long-term stability at 25° C.

| | Composition | | | | | |
|---|---|---|---|---|---|---|
| | Example 1 | | | Comparative Example 1 | | |
| 25° C. | monomers | dimers | polymers | monomers | dimers | polymers |
| $0^{th}$ day | 91.2% | 2.0% | 3.4% | 90.0% | 2.8% | 3.6% |
| 24 months | 86.4% | 4.6% | 4.5% | 71.2% | 17.2% | 5.8% |

The results in Table 1 showed that: in the study on the long-term stability at 25° C., in the docetaxel-albumin nanoparticle composition of Example 1, with the addition of arginine, the content of albumin monomers could be maintained at more than 85% for a long period of time, the content of albumin dimers could be maintained at no more than 5% for a long period of time, and the content of albumin polymers could be maintained at no more than 5% for a long period of time, while in the composition without arginine of Comparative Example 1, the content of albumin monomers was only maintained at about 70%, and the content of albumin dimers and polymers were significantly more than 5%.

Apparently, with the addition of the amino acid of the present invention, particularly arginine, the albumin dimers and polymers in the docetaxel-albumin nanoparticle composition could be significantly reduced, and the albumin monomers were effectively stabilized, the degradation of albumin monomers was substantially avoided, thereby ensuring the safety in clinical application.

TEST EXAMPLE 2

The content of albumin monomers, dimers and polymers in the paclitaxel-albumin nanoparticle compositions prepared according to Example 2 and Comparative Example 2 and in the Abraxane in the long-term stability study thereof under conditions of 24 months storage at 25° C. was determined by the method in Text Example 1. The composition of Example 2 was the paclitaxel-albumin nanoparticle composition comprising arginine, the composition of Comparative Example 2 was the paclitaxel-albumin nanoparticle composition without arginine, and the commercially available Abraxane sample was prepared by the method same as the method for the preparation of the compositions of Example 2 and Comparative Example 2. Test results were shown in Table 2.

TABLE 2

TABLE 2 Content of albumin monomers, dimers and polymers in the composition of Example 2 and Comparative Example 2 in the study on long-term stability at 25° C.

| | Composition | | | | | |
|---|---|---|---|---|---|---|
| | Example 2 | | | Comparative Example 2 | | |
| 25° C. | monomers | dimers | polymers | monomers | dimers | polymers |
| $0^{th}$ day | 92.0% | 4.3% | 1.8% | 91.0% | 4.6% | 2.2% |
| 6 months | 88.7% | 4.5% | 3.4% | 78.0% | 16.2% | 5.8% |
| 12 months | 86.4% | 5.8% | 3.9% | 64.0% | 17.8% | 9.1% |
| 24 months | 84.0% | 7.4% | 4.3% | 58.2% | 20.9% | 11.5% |

In addition, after a storage under the above conditions for 24 months, the contents of albumin monomers, dimers, and polymers in the commercially available Abraxane were 72.6%, 15.2%, and 6.1%, respectively.

The results in Table 2 showed that: in the study on the long-term stability at 25° C., in the paclitaxel-albumin nanoparticle composition, with the addition of arginine, the content of albumin monomers could be maintained at more than 80% for a long period of time, the content of albumin dimers could be maintained at no more than 8% for a long period of time, and the content of albumin polymers could be maintained at no more than 5% for a long period of time, while in Abraxane and the composition without arginine, i.e., the composition of Comparative Example 2, the contents of albumin dimers and polymers were significantly more than 5%, the content of albumin monomers in the Abraxane was only maintained at about 70% of the total amount of the albumins, and the content of albumin monomers in the composition of Comparative Example 2 without arginine was less than 60% of the total amount of the albumins.

Apparently, with the addition of the amino acid of the present invention, particularly arginine, the contents of albumin dimers and polymers in the paclitaxel-albumin nanoparticle composition could be significantly reduced, even the increase of the albumin dimers and polymers during storage could be inhibited, and the albumin monomers were effectively stabilized, the degradation of albumin monomers was substantially avoided, thereby ensuring the safety in clinical application.

TEST EXAMPLE 3

The increase tendency of albumin dimers and polymers in the paclitaxel-albumin nanoparticle compositions prepared according to the methods described in Examples 2 and 3 and Comparative Examples 2 to 4 under accelerated conditions at 60° C. was observed. The contents of albumin monomers, dimers and polymers in the nanoparticle compositions were determined by size exclusion chromatography. The conditions, determination method and calculation manner of the size exclusion HPLC were same as those in Test Example 1. The composition in Example 2 was a paclitaxel-albumin nanoparticle composition comprising arginine, the composition in Example 3 was a paclitaxel-albumin nanoparticle composition comprising histidine, the composition in Comparative Example 2 was a paclitaxel-albumin nanoparticle composition without arginine, the composition in Comparative Example 3 was a paclitaxel-albumin nanoparticle composition comprising glycine, and the composition in Comparative Example 4 is a paclitaxel-albumin nanoparticle composition comprising aspartic acid. Test results were shown in Tables 3-1 and 3-2.

TABLE 3-1

Contents of albumin monomers, dimers and polymers in the compositions of Examples 2-3 and the compositions of Comparative Examples 2-4 under accelerated conditions at 60° C.
60° C.

| | Conditions | | | | | |
|---|---|---|---|---|---|---|
| | 0$^{th}$ day | | | 10$^{th}$ day | | |
| composition | mono-mers | dimers | polymers | mono-mers | dimers | polymers |
| Example 2 | 92.0% | 4.3% | 1.8% | 90.2% | 5.4% | 2.2% |
| Example 3 | 91.8% | 4.3% | 1.9% | 80.1% | 8.3% | 5.8% |
| Comparative Example 2 | 92.0% | 4.1% | 1.9% | 70.6% | 15.9% | 6.8% |
| Comparative Example 3 | 92.2% | 4.5% | 1.7% | 60.8% | 18.2% | 10.5% |
| Comparative Example 4 | 91.9% | 4.0% | 2.5% | 65.3% | 17.6% | 8.6% |

TABLE 3-2

TABLE 3-2 Change in contents of albumin monomers, dimers and polymers in the compositions of Examples 2-3 and the compositions of Comparative Examples 2-4 under accelerated conditions at 60° C.

| Example | Reduced content of albumin monomers | Increased content of albumin dimers | Increased content of albumin polymers |
|---|---|---|---|
| Example 2 | 1.8% | 1.1% | 0.4% |
| Example 3 | 11.7% | 4.0% | 3.9% |
| Comparative Example 2 | 21.4% | 11.8% | 4.9% |
| Comparative Example 3 | 31.4% | 13.7% | 8.8% |
| Comparative Example 4 | 26.6% | 13.6% | 6.1% |

Note:
the reduced content of albumin monomers=the content thereof on the 0$^{th}$ day—the content thereof on the 10$^{th}$ day
the increased content of albumin dimers or albumin polymers=the contents thereof on the 10$^{th}$ day—the contents thereof on the 0$^{th}$ day The results showed that: under the accelerated conditions at 60° C., with the addition of the amino acid having the relative molecular mass defined in the present invention, such as arginine (Example 2) and histidine (Example 3), the contents of albumin polymers and albumin dimers in the albumin nanoparticle compositions were maintained at less than 6% and 9% of the total amount of the albumins, respectively, the contents were significantly lower than that of albumin polymers and albumin dimers in the composition without arginine (Comparative Example 2), and the compositions comprising an amino acid having a relative molecular mass not fall in 145-175 such as glycine (Comparative Example 3) and aspartic acid (Comparative Example 4). Further, the increased amounts of albumin polymers and dimers in the compositions of Examples 2 and 3 of the present invention were also significantly lower than those in the compositions of Comparative Examples 2-4, meanwhile, the changed amounts of albumin monomers in the compositions of Examples 2 and 3 of the present invention were also significantly lower than that in the compositions of Comparative Examples 2-4. These results demonstrated that, under same conditions, the addition of the amino acid of the present invention could significantly reduce the increase of albumin dimers and polymers and effectively stabilize albumin monomers in the albumin nanoparticle composition, keep albumin monomers from being degraded substantially, thereby ensuring the safety in clinical application.

TEST EXAMPLE 4

The contents of albumin monomers, dimers and polymers in the cabazitaxel-albumin nanoparticle composition comprising arginine hydrochloride obtained in Example 4 and in the cabazitaxel-albumin nanoparticle compositions of Comparative Examples 5-7 were determined under the accelerated conditions at 60° C. by using the same method as in Test Example 3. Test results were shown in Table 4.

TABLE 4

TABLE 4 Contents of albumin monomers, dimers and polymers in the composition of Example 4 and in the compositions of Comparative Examples 5-7 at 60° C.
60° C.

| | Conditions | | | | | |
|---|---|---|---|---|---|---|
| | 0$^{th}$ day | | | 10$^{th}$ day | | |
| composition | mono-mers | dimers | polymers | mono-mers | dimers | polymers |
| Example 4 | 93.4% | 4.2% | 1.2% | 91.6% | 4.8% | 1.8% |
| Example 5 | 93.1% | 4.1% | 1.4% | 71.2% | 16.4% | 6.2% |
| Example 6 | 92.8% | 4.1% | 1.6% | 76.6% | 13.6% | 4.9% |
| Example 7 | 92.5% | 4.3% | 1.6% | 73.8% | 15.2% | 5.5% |

Apparently, with the addition of arginine hydrochloride, in the cabazitaxel-albumin nanoparticle composition of Example 4 of the present application, the contents of albumin dimers and polymers were significantly lower than those in the corresponding composition without the addition of arginine hydrochloride (Comparative Example 5), the composition with the addition of sodium octanoate (Comparative Example 6) and the composition with the addition of sodium octanoate and acetyl tryptophan (Comparative Example 7), the increased amounts of albumin dimers and polymers were also significantly lower than those in the corresponding composition without the salt of amino acid of the present invention, the composition with the addition of sodium octanoate and the composition with the addition of sodium octanoate and acetyl tryptophan, and the degradation rate of albumin monomers was significantly lower than that in the corresponding composition without the salt of amino acid having a relative molecular mass of 145-175 of the present invention, the composition with the addition of sodium octanoate and the composition with the addition of sodium octanoate and acetyl tryptophan. These results demonstrated that, under same conditions, the addition of the salt of amino acid of the present invention could effectively inhibit the increase of albumin dimers and polymers.

TEST EXAMPLE 5

The contents of albumin monomers, dimers and polymers in the cabazitaxel-albumin nanoparticle composition comprising arginine hydrochloride obtained in Example 4 and in the cabazitaxel albumin nanoparticle composition without arginine hydrochloride obtained in Comparative Example 5 were determined under the accelerated conditions at 40° C. by using the same method as in Test Example 3. The test results were shown in Table 4.

TABLE 5

TABLE 5 Contents of albumin monomers, dimers and polymers in the composition of Example 4 and in the composition of Comparative Example 5 at 40° C.

| Condition 40° C. | Composition | | | | | |
|---|---|---|---|---|---|---|
| | Example 4 | | | Example 5 | | |
| | monomers | dimers | polymers | monomers | dimers | polymers |
| 0 month | 93.4% | 4.2% | 1.2% | 93.1% | 4.1% | 1.4% |
| 1 month | 92.8% | 4.3% | 1.5% | 86.6% | 7.0% | 3.2% |
| 3 months | 91.5% | 4.6% | 2.0% | 79.2% | 10.4% | 5.2% |
| 6 months | 90.8% | 4.9% | 2.2% | 74.6% | 14.2% | 5.6% |

In summary, the above results showed that, the addition of an amino acid having a relative molecular mass of 145-175 or a salt thereof to a nanoparticle composition comprising a taxane compound could effectively inhibit the increase of albumin dimers and polymers and the degradation of albumin monomers in the composition, control the contents of albumin monomers, dimers and polymers in the composition, and effectively stabilize albumin monomers therein, and the albumin stabilizing effect thereof was superior to commonly used albumin stabilizers, keep albumin monomer from being degraded substantially, to ensure the safety in clinical application.

In addition to those described herein, according to the above descriptions, various modifications of the invention will be obvious for a person skilled in the art. Such modifications also fall within the scope of the appended claims.

Each of the references (including all patents, patent applications, journal articles, books, and any other publications) cited in this application is hereby incorporated by reference in its entirety.

What is claimed is:

1. A stable albumin containing pharmaceutical composition, comprising (i) an albumin and (ii) at least one amino acid selected from arginine, histidine and lysine;
   wherein the amino acid or the salt thereof and albumin are present in a weight ratio ranging from 0.1:1 to 10:1;
   wherein the amount of albumin dimers present in said pharmaceutical composition after the pharmaceutical composition is stored for at least one year constitute no more than 10% of the total amount of the albumins contained in the pharmaceutical composition.

2. The albumin containing pharmaceutical composition according to claim 1, wherein the amount of albumin dimers present in said pharmaceutical composition after the pharmaceutical composition is stored for at least one year constitute no more than 6% of the total amount of the albumins contained in the pharmaceutical composition.

3. The albumin containing pharmaceutical composition according to claim 1, wherein, the pharmaceutical composition comprises a taxane compound as an active ingredient.

4. The albumin containing pharmaceutical composition according to claim 3, wherein the taxane compound is selected from the group consisting of paclitaxel, docetaxel, cabazitaxel, and derivatives thereof.

5. The albumin pharmaceutical composition according to claim 1, wherein the amino acid is arginine.

6. The albumin containing pharmaceutical composition according to claim 1, wherein the amino acid or the salt thereof and albumin are present in a weight ratio ranging from 0.2:1 to 5:1.

* * * * *